(12) United States Patent
Curtis

(10) Patent No.: US 6,981,992 B2
(45) Date of Patent: Jan. 3, 2006

(54) THREE PRONG ADAPTER

(75) Inventor: Michael J. Curtis, Green Bay, WI (US)

(73) Assignee: American Prosthetic Components, Inc., Green Bay, WI (US)

( * ) Notice: Subject to any disclaimer, the term of this patent is extended or adjusted under 35 U.S.C. 154(b) by 19 days.

(21) Appl. No.: 10/409,457

(22) Filed: Apr. 9, 2003

(65) Prior Publication Data

US 2004/0204770 A1   Oct. 14, 2004

(51) Int. Cl.
*A61F 2/60*   (2006.01)

(52) U.S. Cl. ...................................... 623/33
(58) Field of Classification Search ............ 623/33–37, 623/57

See application file for complete search history.

(56) References Cited

U.S. PATENT DOCUMENTS

| | | | |
|---|---|---|---|
| 1,272,179 A | * | 7/1918 | Anderson et al. ............. 623/60 |
| 5,458,657 A | | 10/1995 | Rasmusson |
| 6,013,105 A | | 1/2000 | Potts |
| 6,692,533 B2 | * | 2/2004 | Johnson et al. ............... 623/47 |
| 2003/0195636 A1 | * | 10/2003 | Coop ........................... 623/36 |

OTHER PUBLICATIONS

American Prosthetic Components, Inc. Informational brouchure (Jan. 2003) p. 3 of 4.

* cited by examiner

Primary Examiner—Alvin J. Stewart
(74) Attorney, Agent, or Firm—Brannen Law Office, LLC

(57) ABSTRACT

The present invention has three arcuate prongs that are connected to a hub. The hub has a first end and a second end, and at least one end of the hub is circumferentially continuous. The hub second end is threaded. In one embodiment, the hub has a threaded outer surface. In another embodiment, the hub has a threaded inner surface. The prongs are manipulable, or bendable. Stress developed during manipulation of the prongs does not distort the threaded surface of the hub second end. An additional component can be threadably connected to the threaded surface of the hub second end. The circumferentially continuous portion of the hub acts as a barrier that prevents any excess laminate from contacting and bonding with the threads.

25 Claims, 15 Drawing Sheets

FIG. 1 BACKGROUND MATERIAL

THREE PRONG ADAPTER

BACKGROUND OF THE INVENTION

1. Field of the Invention

The present invention relates generally to the field of prosthetics, and more particularly to a three prong adapter having a hub with an end having a threaded outer surface and is used to interconnect a socket made for a stump of a residual limb and a prosthetic limb.

2. Description of the Related Art

Sometimes, due to accidents, health problems, birth defects, etc., people 5 need to have a limb 6 amputated. The amputated limb 6 terminates in a stump 7. In general, a socket 10 can be formed for a particular stump 7. Those sockets are well known in the art, and each socket 10 has a central axis 11. An adapter is needed to connect the socket to a prosthetic limb.

Fortunately for people requiring a prosthetic limb, many advancements have been made in the field of prosthetic limbs. Patients now have many choices, including endoskeletal and exoskeletal prosthetic limbs. The present invention relates to endoskeletal prosthetic limbs. That is, limbs comprised of structural components and an optional aesthetic outer shell. Several examples of available prosthetic devices are described below.

U.S. Pat. No. 5,458,657 to Rasmusson shows an endoskeletal prosthesis having an adapter assembly. The adapter assembly has a socket coupler embedded within a stump socket. The socket coupler appears generally cup shaped, and appears to have limited ability to adjust to fit with stumps of various sizes. This socket coupler therefore has an undesirable limited practicality. A socket adapter plate is bolted to a bottom side of the socket coupler. The interface between the socket coupler and socket adapter is flat, and that interface lies generally in a plane that is perpendicular to the socket longitudinal axis. Those bolts must be able to withstand and transfer any shear stress between the socket adapter and the socket coupler in the direction generally perpendicular to the socket longitudinal axis. Yet, those bolts may not be designed to withstand large amounts of shear stress.

U.S. Pat. No. 6,013,105 to Potts shows a prosthesis connector and alignment assembly having a rotational positioning module and sliding adjustment. The base is shown as a plate having an annular wall projecting from the plate with external threads. A locking assembly threads onto the threaded annular wall of the base plate. This design is undesirably complicated. Further, no external threads are shown to mate with a separate prosthetic component. The plate only engages the bottom of the socket, which results in a less than optimum structural connection, as the fasteners that connect the plate to the socket have to withstand any and all shear stress between the socket and the plate.

Three prong adapters in existence, such as the one shown in FIG. 1, solve many of the problems associated with the above-described patents. The three prong adapters in existence are relatively simple in design, and are structurally strong while at the same time light weight. One such three prong adapter is sold by American Prosthetic Components Inc., under model number APC-700L. FIG. 1 is representative of this type of adapter. As shown in FIG. 1, existing three prong adapters 20 have three prongs 21. A hole extends through the three prong adapter 20. The hole 22 has a wall 25 with a partition 26. Threads 27 are on the inside of the wall 25. The threads 27 on the inside of the wall 25 are partitioned in a manner that corresponds to the wall partition 26, such that the threads have respective first ends 28 and second ends 29. A clamp 35 is on the outside of the three prongs adapter. A screw 36 can be turned into the clamp 36 to reduce the size of the partition 26 and reduce the circumferential size of the adapter 20 to tighten down on a component threaded into the adapter.

The adapter prongs 21 are used to connect to the lower sides of the socket. One major advantage of a three prong adapter over a plate with a flat interface is that the prongs 21 provide an improved structural connection to a socket compared to a plate, especially in directions perpendicular to a central axis 11 of the socket 10, such as the in lateral and medial directions 15 and 16, respectively, as well as in the anterior and posterior directions 17 and 18, respectively. In this regard, the bolts or laminate do not have to withstand the shear stress in directions perpendicular to the central axis 11 of the socket 10.

A further advantage of the now existing three prong adapters 20 over the other adapters described above is that one or more of the prongs 21 can be bent so that the three prong adapter 20 can better fit with a given socket.

The existing three prong adapters 20 perform well in some circumstances. Yet, even the existing three prong adapters 20 can be improved upon. The wall 25 is completely partitioned to allow the clamp 35 to be able to selectively reduce the size of the hole after an object is threaded into it. This is done in order to clamp down on an object threaded into the adapter 20. However, when one or more prongs 21 are manipulated, or bent, to enable the three prong adapter 20 to better fit on the socket, the threads 27 can become misaligned along the partition 26. When this happens, it can be difficult or impossible to thread an object into the three prong adapter 20.

A further undesirable complication of using the existing three prong adapters is that the laminate used to connect the three prong adapter 20 to a socket 10, which is well known in the art, can sometimes flow into contact with and bond to the threads 27. When this occurs, a prosthetic component may not properly thread into the three prong adapter 20. It is difficult and sometimes impossible to satisfactorily remove laminate that is bonded to the threads 27.

Thus, there exists a need for a three prong adapter that maintains the advantages of the existing three prong adapters, but that also solves these and other problems associated with existing three prong adapters.

SUMMARY OF THE INVENTION

The present invention is used in the field of prosthetics, and more particularly used to connect a prosthetic limb to a socket.

The present invention has three prongs. The prongs have an arcuate shape, and are connected to a hub. The prongs extend in a first direction away from a first end of the hub. In one embodiment of the present invention, the hub has a second end with a threaded outer surface. At least one portion of the hub is circumferentially continuous.

The prongs are manipulable such that the three prong adapter can be adjusted for use with a particular socket. However, stress developed during manipulation of the prongs does not distort the threaded outer surface of the second end of the hub. That is, the portion of the hub that is circumferentially continuous prevents the internal stresses that cause the existing three prong adapters to distort and misalign from affecting the threaded outer surface of the second end of the hub of the present invention. The prongs can be bolted and/or laminated to the stump.

In another aspect of the present invention, an additional component can be threaded onto the threaded outer surface of the second hub end. That component can itself have a hole similar to the hole of existing three prong adapters. Therefore, the present invention can be used with all systems that currently use an existing three prong adapter.

In an additional embodiment of the present invention, the hub second end has a bore with a threaded inside surface. In this embodiment, the hub second end is separated from the hub first end by at least one slit through the hub partially around the hub circumference. The threaded inside surface has a partition, such that a clamp can be tightened to selectively reduce the circumference of the hub second end and tighten the hub second end around a prosthetic component that is threaded into the hub second end. The first hub end in this embodiment is circumferentially continuous. In this regard, the first end of the hub prevents any stresses developed during manipulation of the prongs from distorting the alignment of the threads.

According to yet another aspect of the present invention, laminate that is used to connect the three prong adapter to the socket is prevented from contacting and bonding to the threads of the adapter. The circumferentially continuous portion of the hub separates the threads of the second end of the adapter from the first end of the hub, thereby preventing the laminate from flowing into and bonding with the threads.

Other advantages, benefits, and features of the present invention will become apparent to those skilled in the art upon reading the detailed description of the invention and studying the drawings.

DETAILED DESCRIPTION OF THE PREFERRED EMBODIMENTS

Figure 1:
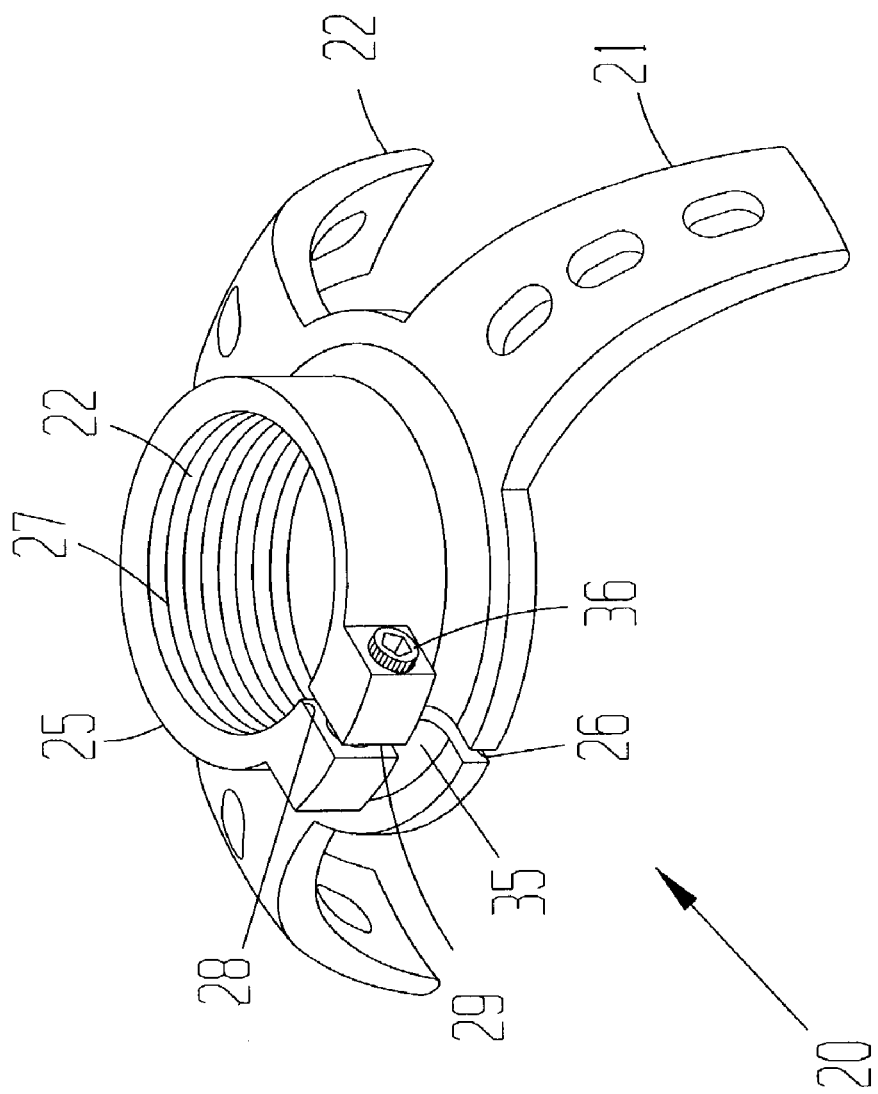
FIG. 1 is a perspective view of an existing three prong adapter, showing a split through the entire hub.

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

The present invention relates to and comprises a three prong adapter 50. The three prong adapter 50 is preferably made of titanium alloy or steel. However, any other materials that are strong, yet light weight, can be used without departing from the broad aspects of the present invention. The three prong adapter 50 is preferably precision manufactured with a Computer Numerical Control, or CNC, machine.

In one embodiment of the present invention, as shown in FIGS. 4–10, the three prong adapter 50 has a hub 60 that defines a central axis 61. The hub 60 has a first end 62 and a second end 63. The second end 63 has an outer surface 64 containing threads 65. At least one of the first and second ends 62 and 63 has a circumferentially continuous portion 66. However, it is preferred that at least the second end 63 is circumferentially continuous. Further, it is preferred that the threads 65 are continuous around the outer surface 64 of the second end 63 of the hub 60. The second end 63 of the hub 60 is preferably round and has a hollow core. The thickness of the hub 60 between the outer surface 64 and the core only needs to be large enough to provide a desired amount of strength to the second end 63 of the hub. The first end 62 of the hub also preferably has a hollow core. The first end 62 of the hub 60 is preferably round in shape.

Figure 6:
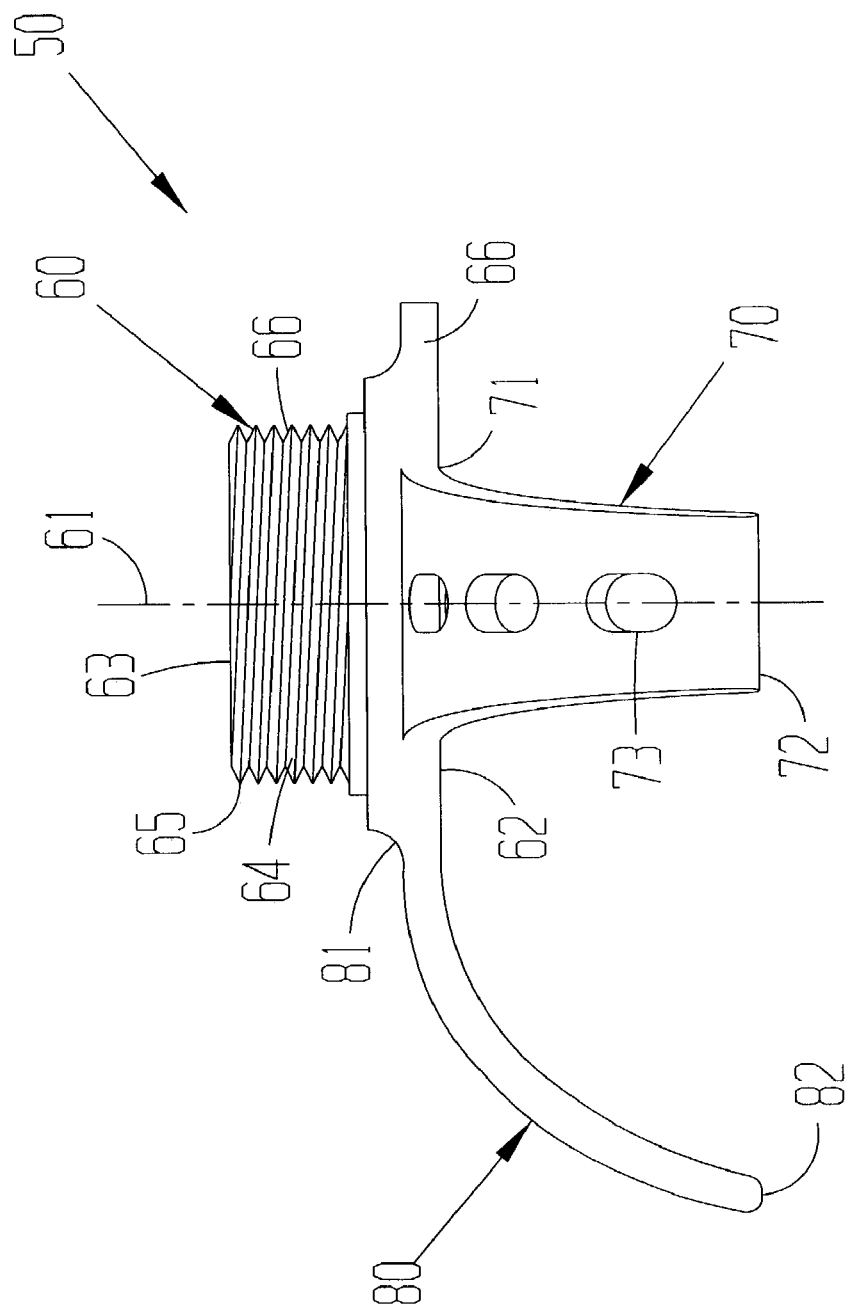
FIG. 6 is a side view of FIG. 4.
Figure 7:
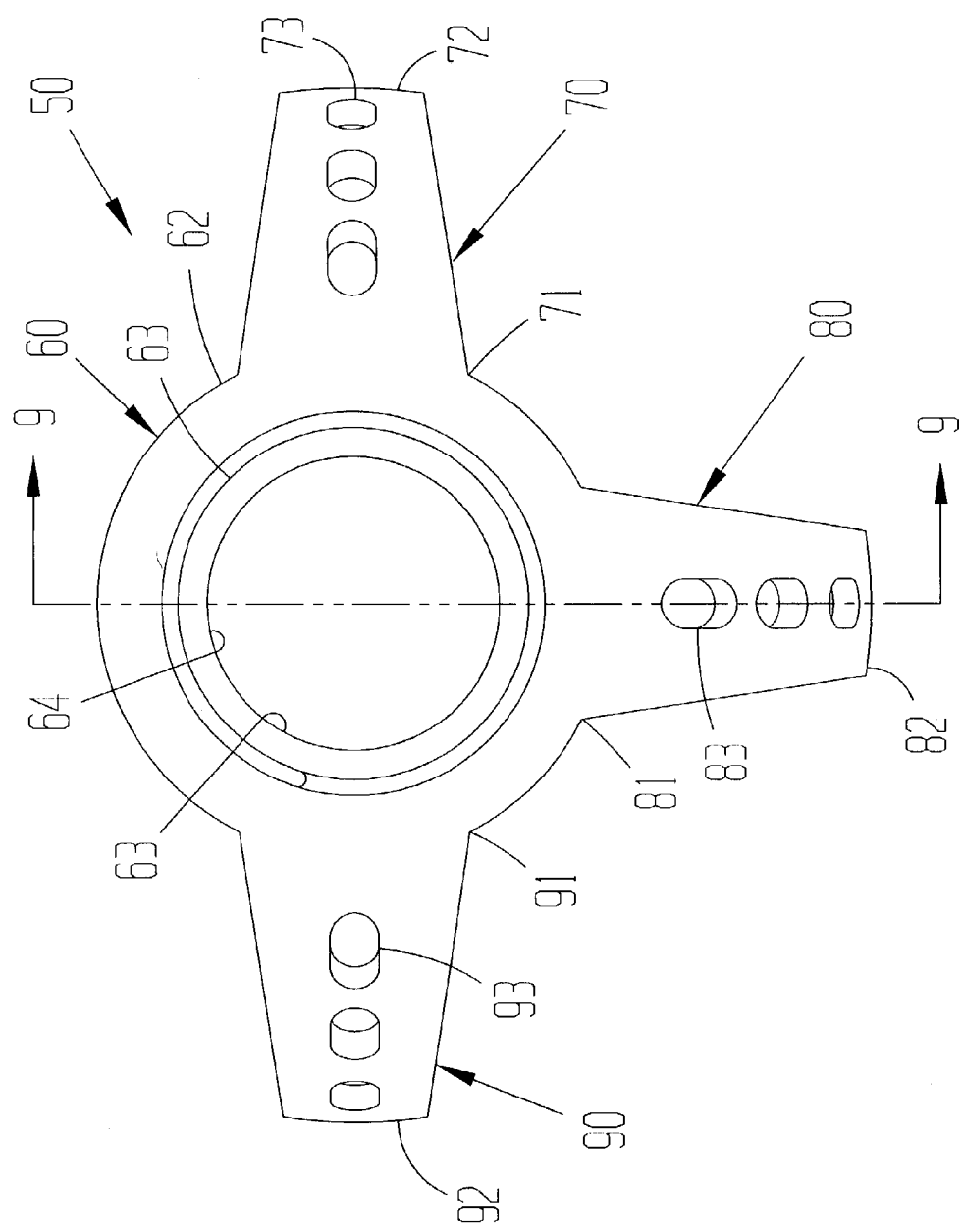
FIG. 7 is a top view of FIG. 4.
Figure 8:
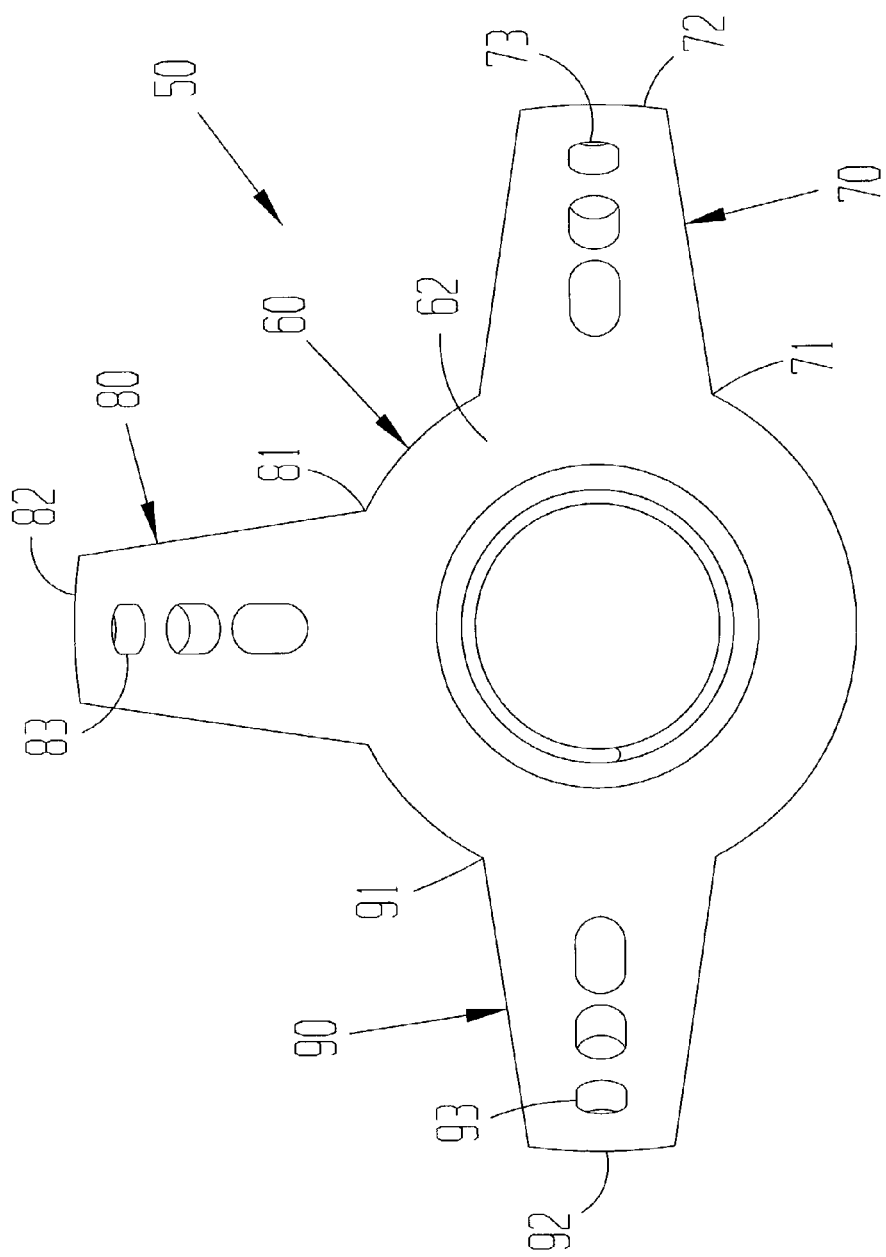
FIG. 8 is a bottom view FIG. 4.
Figure 9:
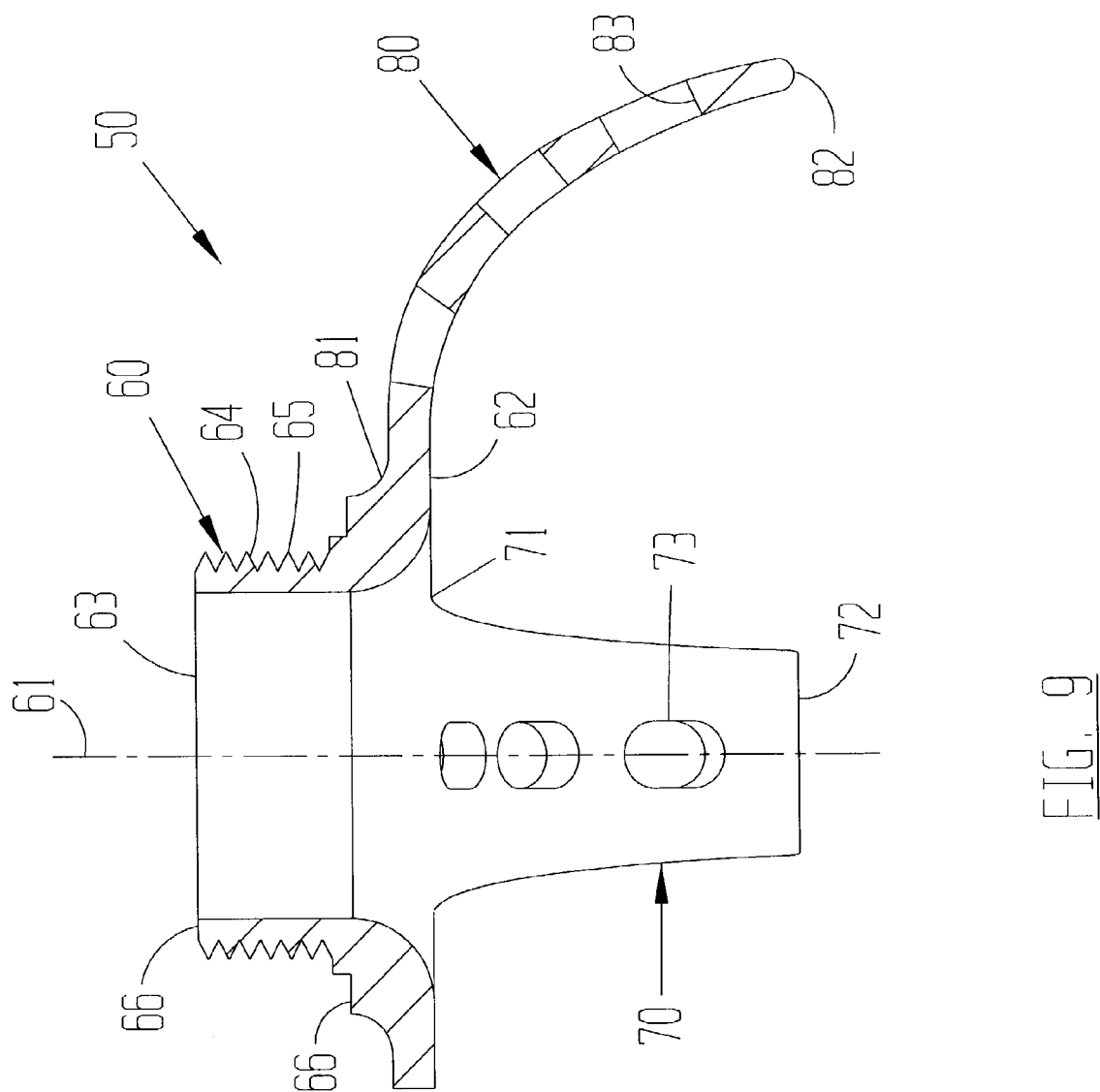
FIG. 9 is a cross-sectional view of the present invention taken along line 9—9 in FIG. 7.

In a preferred embodiment of the present invention shown in FIG. 6, the hub second end 63 has an outer diameter of approximately 1.5 inches. However, other outer diameters can be used without departing from the broad aspects of the present invention. Also, the threads 65 wrap around the outer surface 64 approximately 7 or 8 times. In this regard, the thread length is approximately 0.3 inches. However, the threads 65 could wrap around the outer surface 64 greater or fewer times, and the thread length can correspondingly be longer or shorter without departing from the broad aspects of the present invention.

Figure 5:
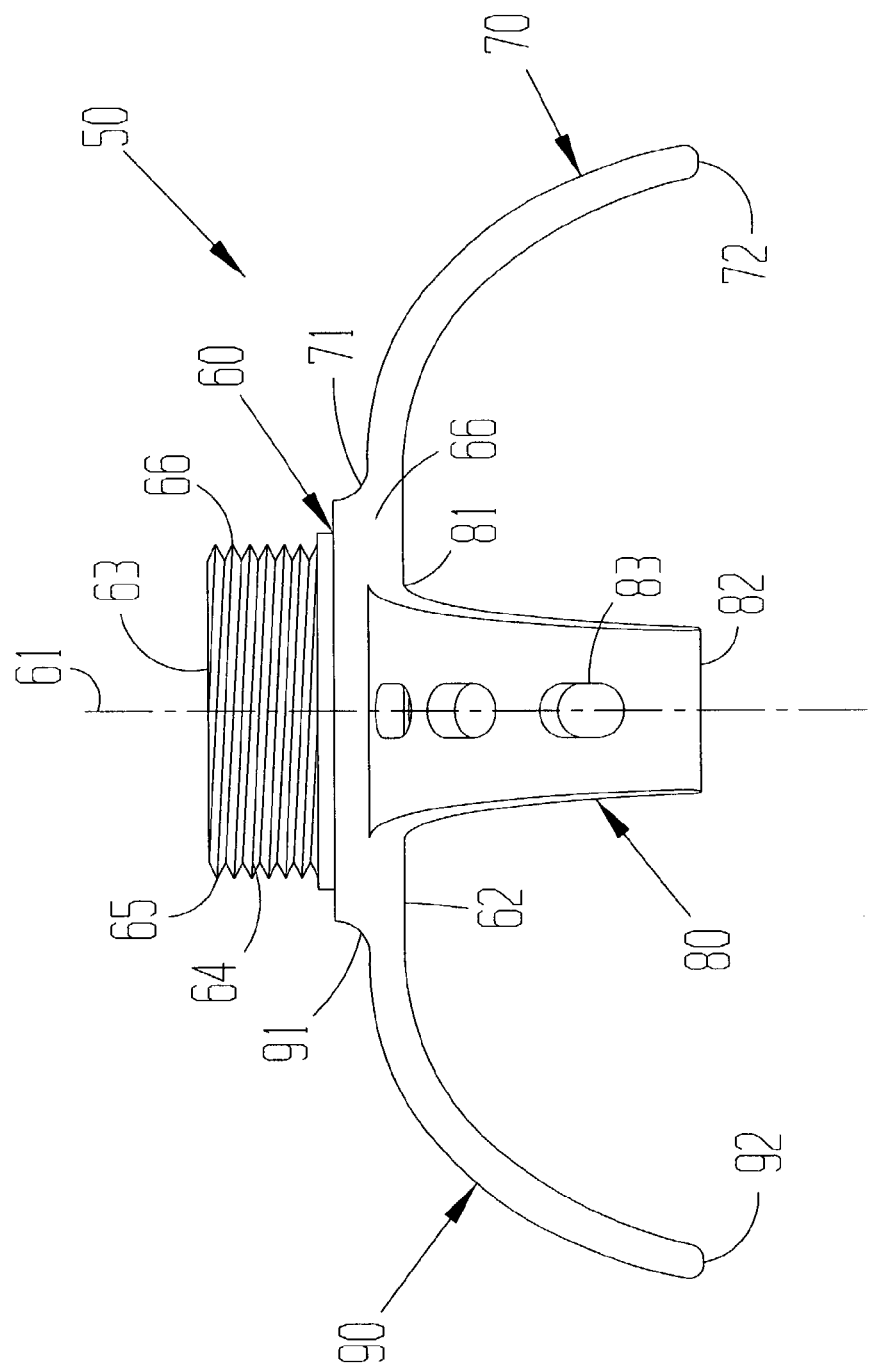
FIG. 5 is a rear view of FIG. 4.
Figure 10:
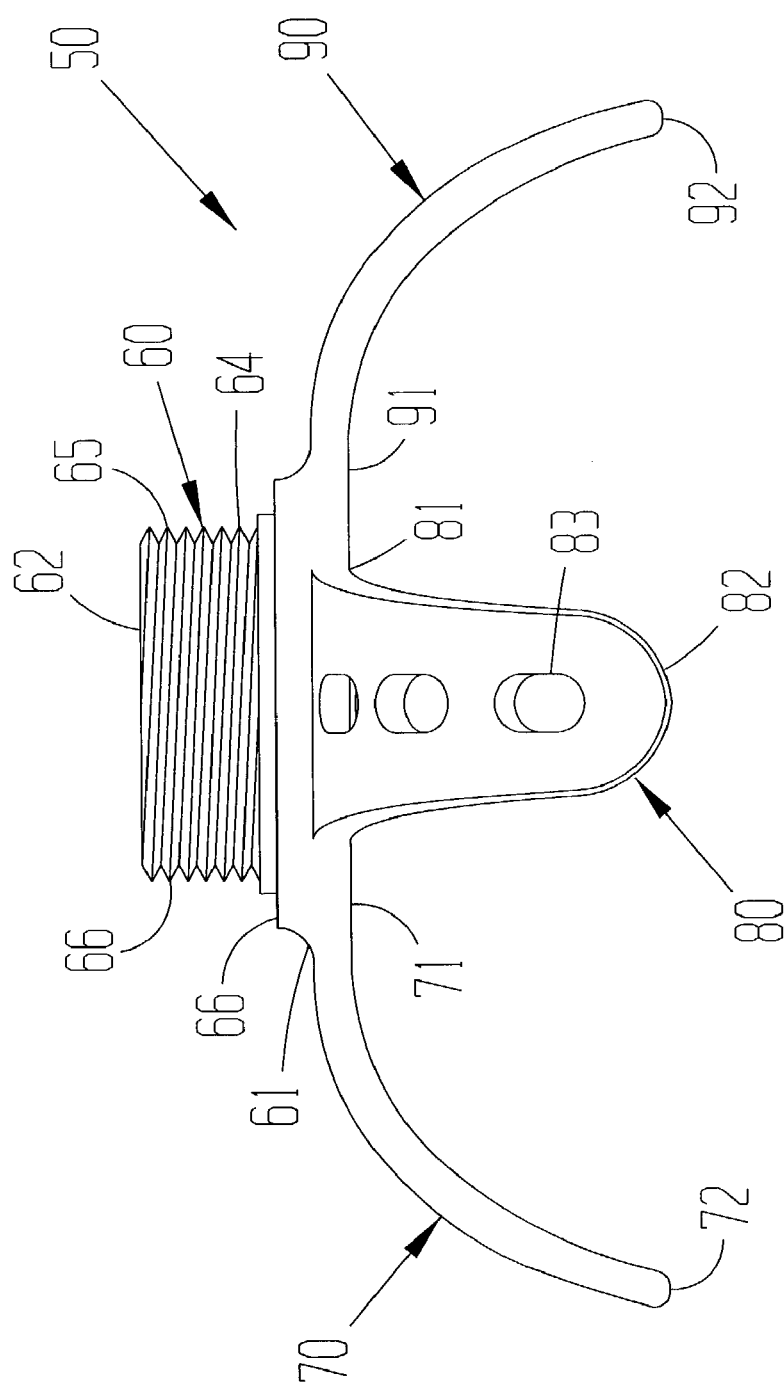
FIG. 10 is similar to FIG. 5, but shows an alternative embodiment of the present invention having prongs with rounded ends.
Figure 11:
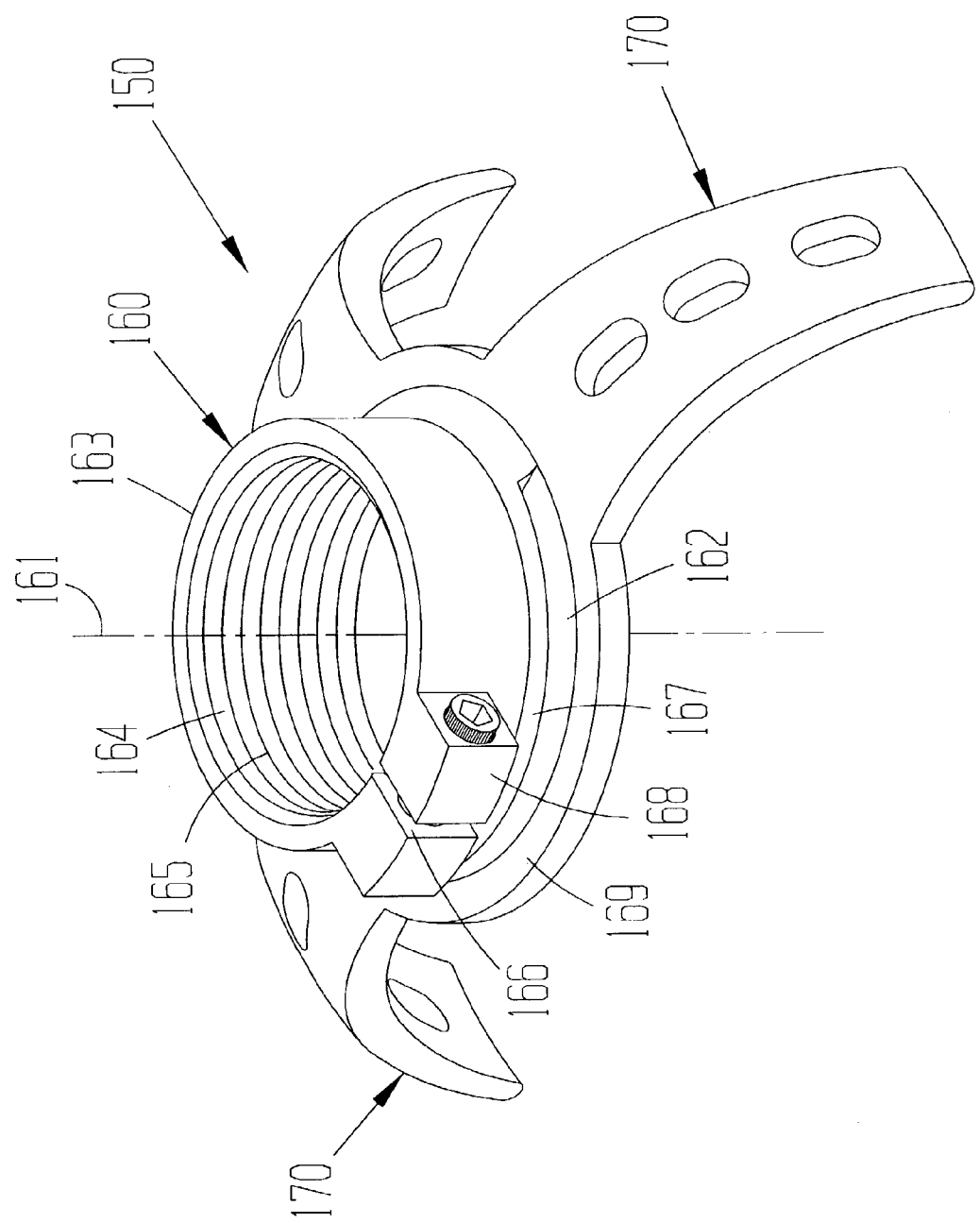
FIG. 11 is a perspective view of an alternative embodiment of the present invention showing the hub second end having a threaded inner surface.
Figure 12:
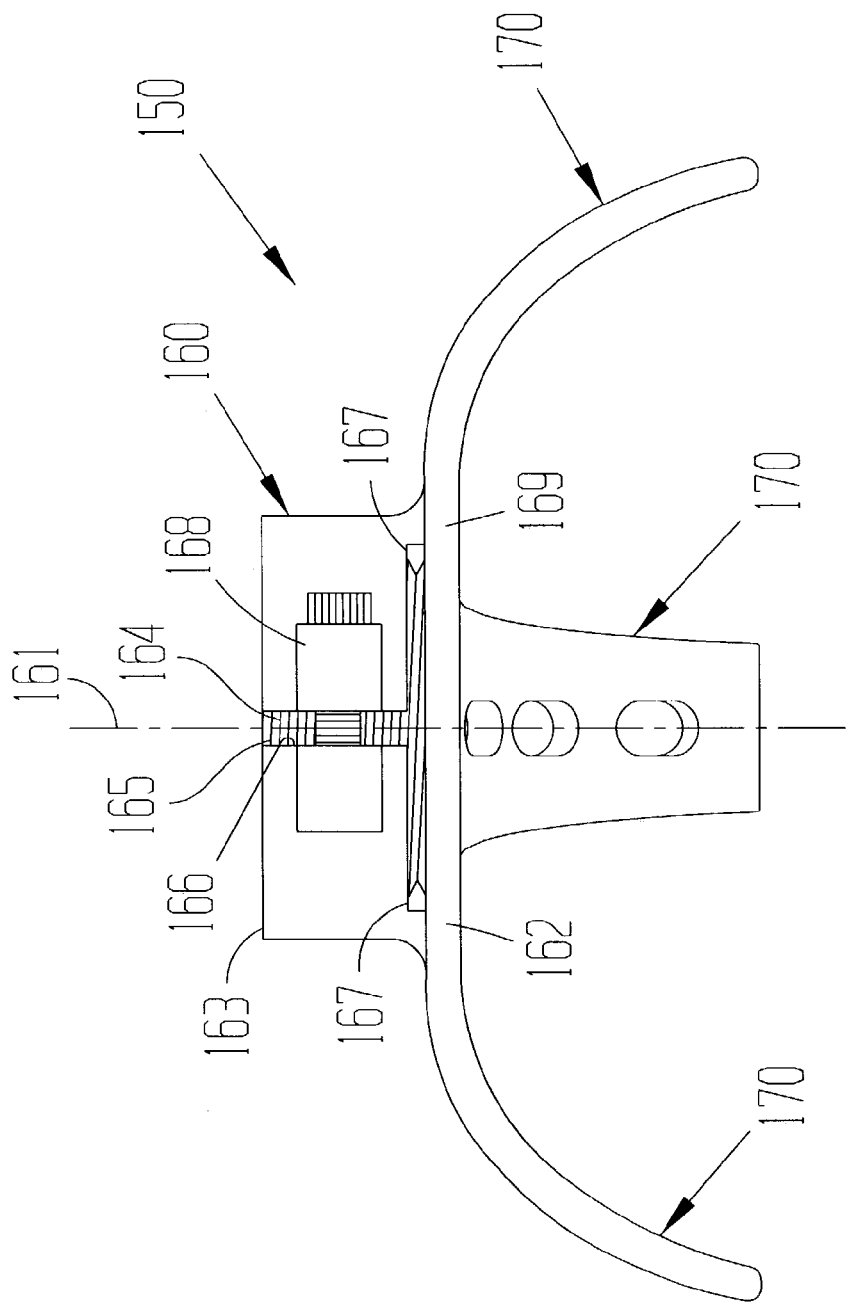
FIG. 12 is a front view of FIG. 11.
Figure 13:
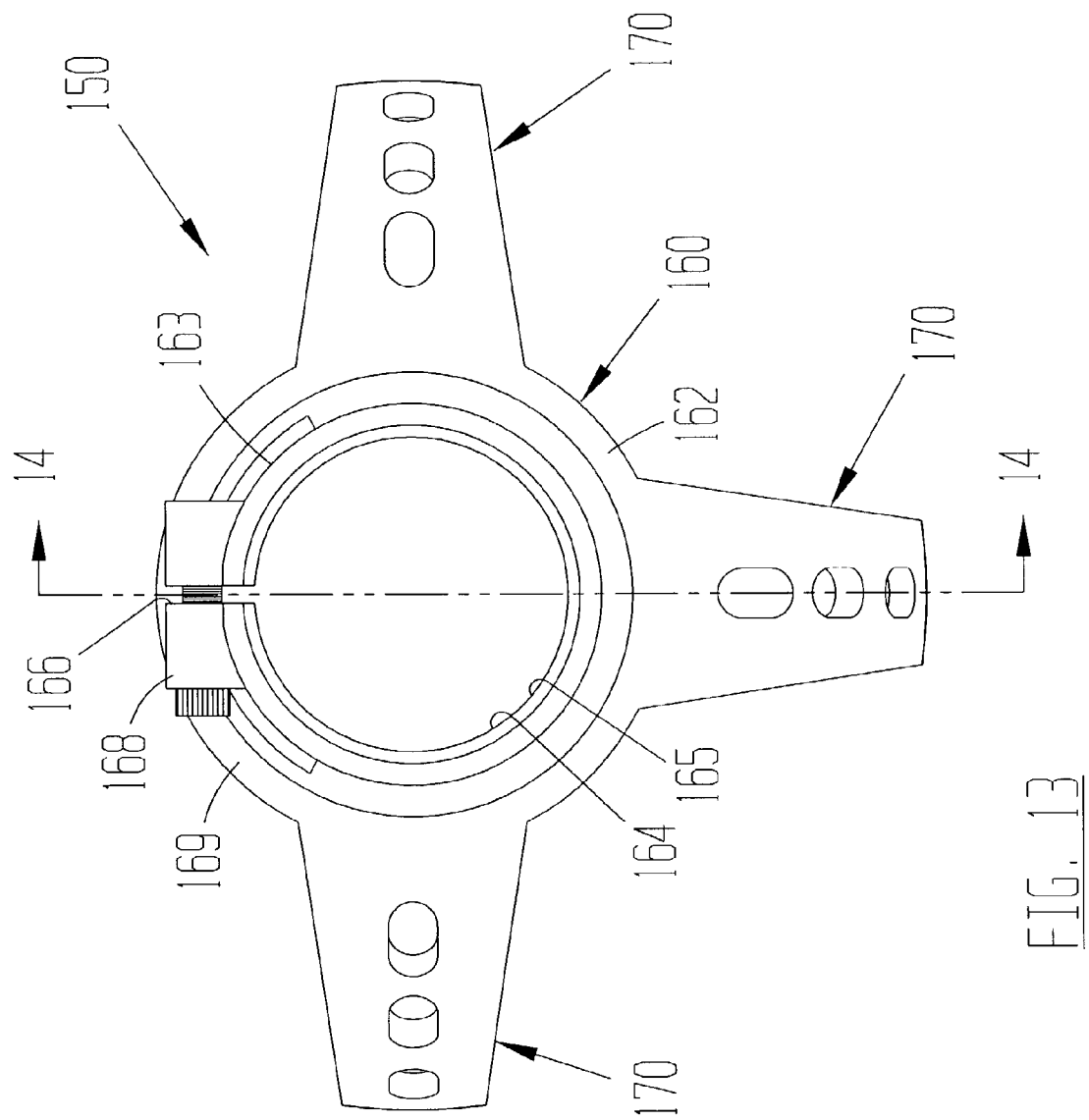
FIG. 13 is a top view of FIG. 11.
Figure 14:
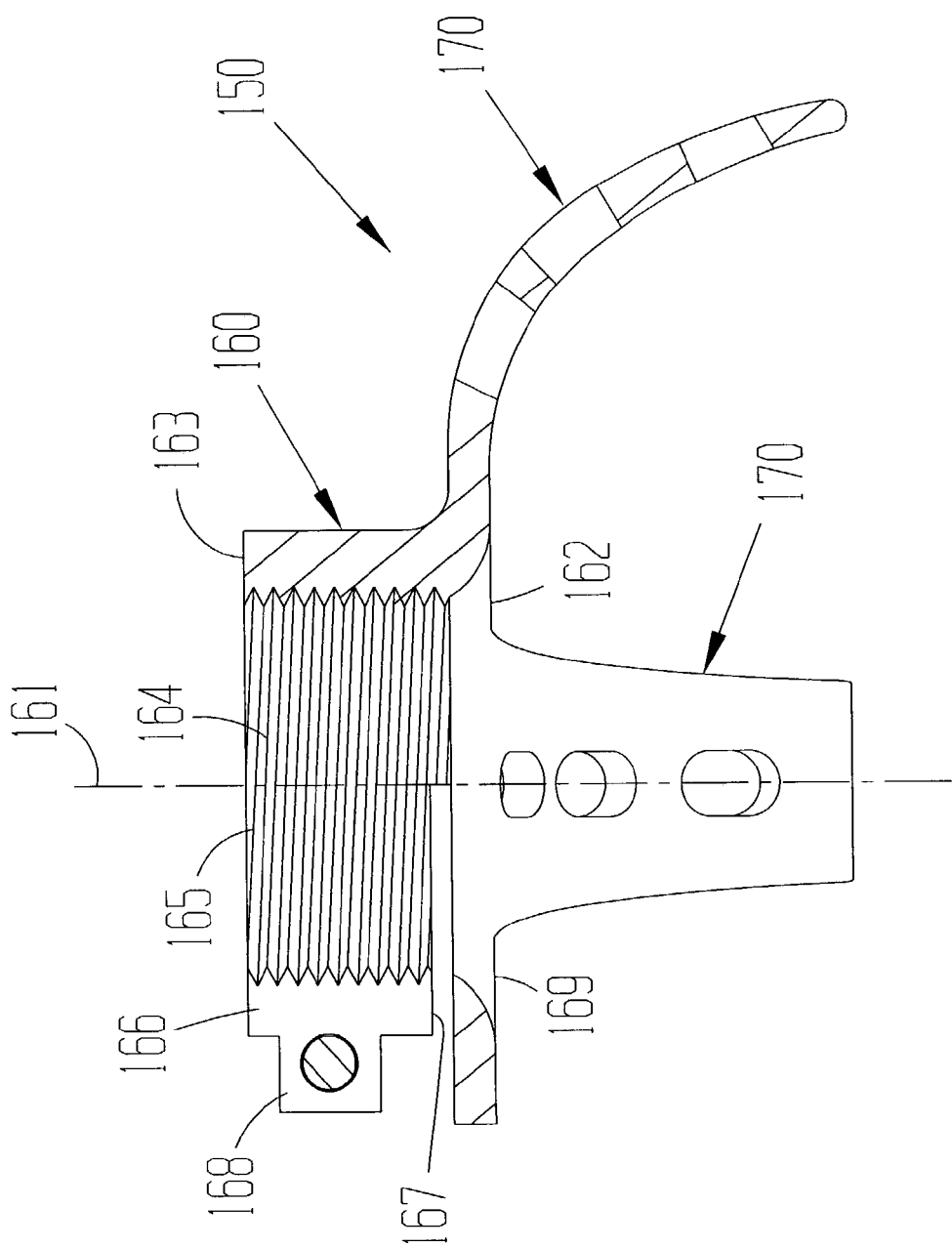
FIG. 14 is a cross-sectional view taken along line 14—14 in FIG. 13.

A first prong 70 has a connected end 71 connected to the hub 60 and a free end 72, or distal end, remote from the hub 60. The connected end 71 is preferably connected to the first end 62 of the hub. Further, the first prong 61 is preferably formed integral with the first end 62 of the hub. One or more holes 73 are through the first prong 70 intermediate between the connected end 71 and the free end 72. The first prong 70 is preferably arcuate shaped, such that the free end 72 extends away from first end 62 of the hub in a path that becomes increasingly closer to parallel with the central hub axis 61 near the free end 72. The free end 72 of the first prong 70 is manipulable, or bendable, with respect to the connected end 71 of the prong. The free end 72 of the first prong 70 can be squared, as shown in FIG. 5, or can be rounded, as shown in FIG. 10.

A second prong 80 also has a connected end 81 connected to the hub 60 and a free end 82, or distal end, remote from the hub 60. The connected end 81 is preferably connected to the first end 62 of the hub. Further, the second prong 80 is preferably formed integral with the first end 62 of the hub. One or more holes 83 are through the second prong 80 intermediate between the connected end 81 and the free end 82. The second prong 80 is preferably arcuate shaped, such that the free end 82 extends away from first end 62 of the hub 60 in a path that becomes increasingly closer to parallel with the central hub axis 61 near the free end 82. The free end 82 of the second prong 80 is manipulable, or bendable, with respect to the connected end 81 of the prong. The free end 82 of the second prong 80 can be squared, as shown in FIG. 5, or can be rounded, as shown in FIG. 10.

A third prong 90 also has a connected end 91 connected to the hub 60 and a free end 92, or distal end, remote from the hub 60. The connected end 91 is preferably connected to the first end 62 of the hub. Further, the third prong 90 is preferably formed integral with the first end 62 of the hub. One or more holes 93 are through the third prong 90 intermediate between the connected end 91 and the free end 92. The second prong 90 is preferably arcuate shaped, such that the free end 92 extends away from first end 62 of the hub 60 in a path that becomes increasingly closer to parallel with the central hub axis 61 near the free end 92. The free end 92 of the second prong 90 is manipulable, or bendable, with respect to the connected end 91 of the prong. The free end 92 of the third prong 90 can be squared, as shown in FIG. 5, or can be rounded, as shown in FIG. 10.

As best shown in FIGS. 4, 5, 7 and 8, the first prong 70 and third prong 90 are preferably diametrically opposed around the perimeter of the first hub end 62. The second prong 80 is intermediate between the first prong 70 and third prong 90.

Figure 2:
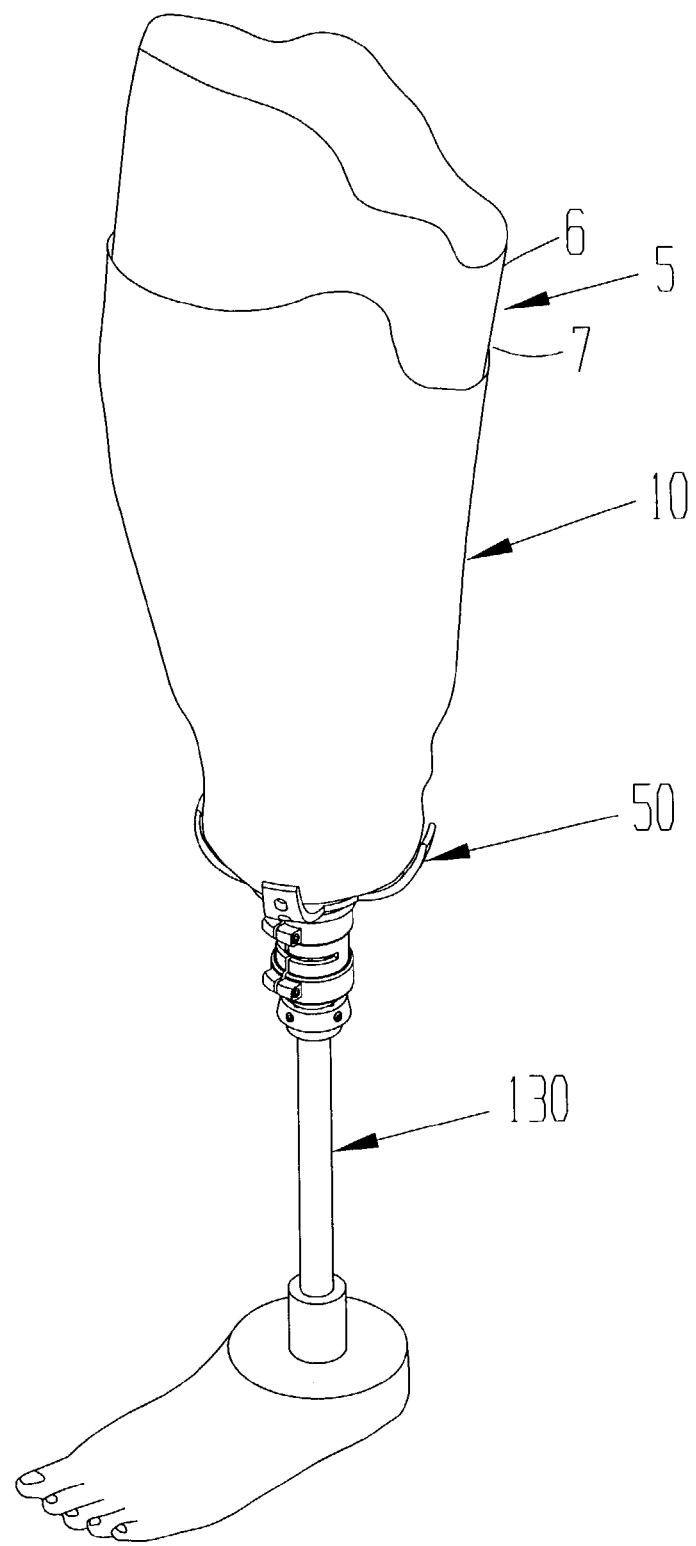
FIG. 2 is a perspective view of the present invention secured on a socket and showing a prosthetic limb attached to the adapter.
Figure 3:
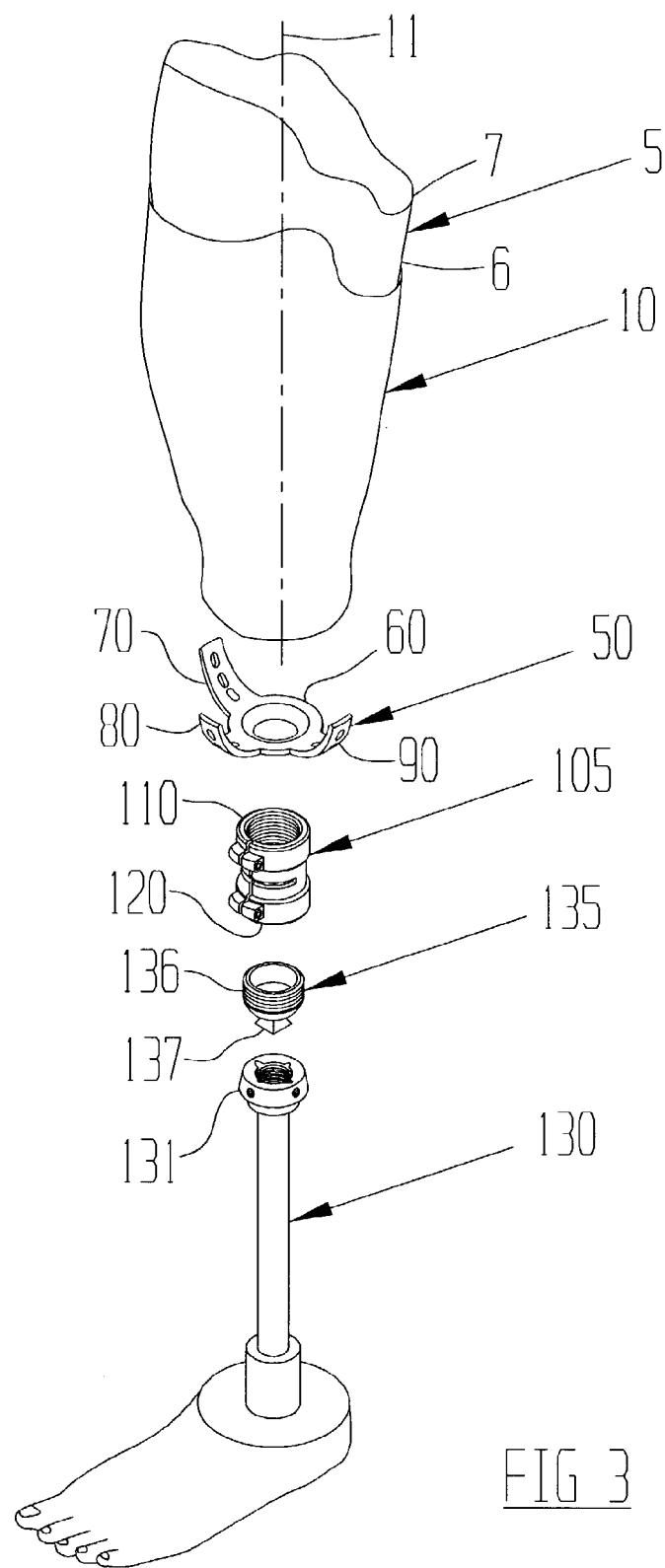
FIG. 3 is a partial exploded view of the present invention shown in FIG. 2.
Figure 4:
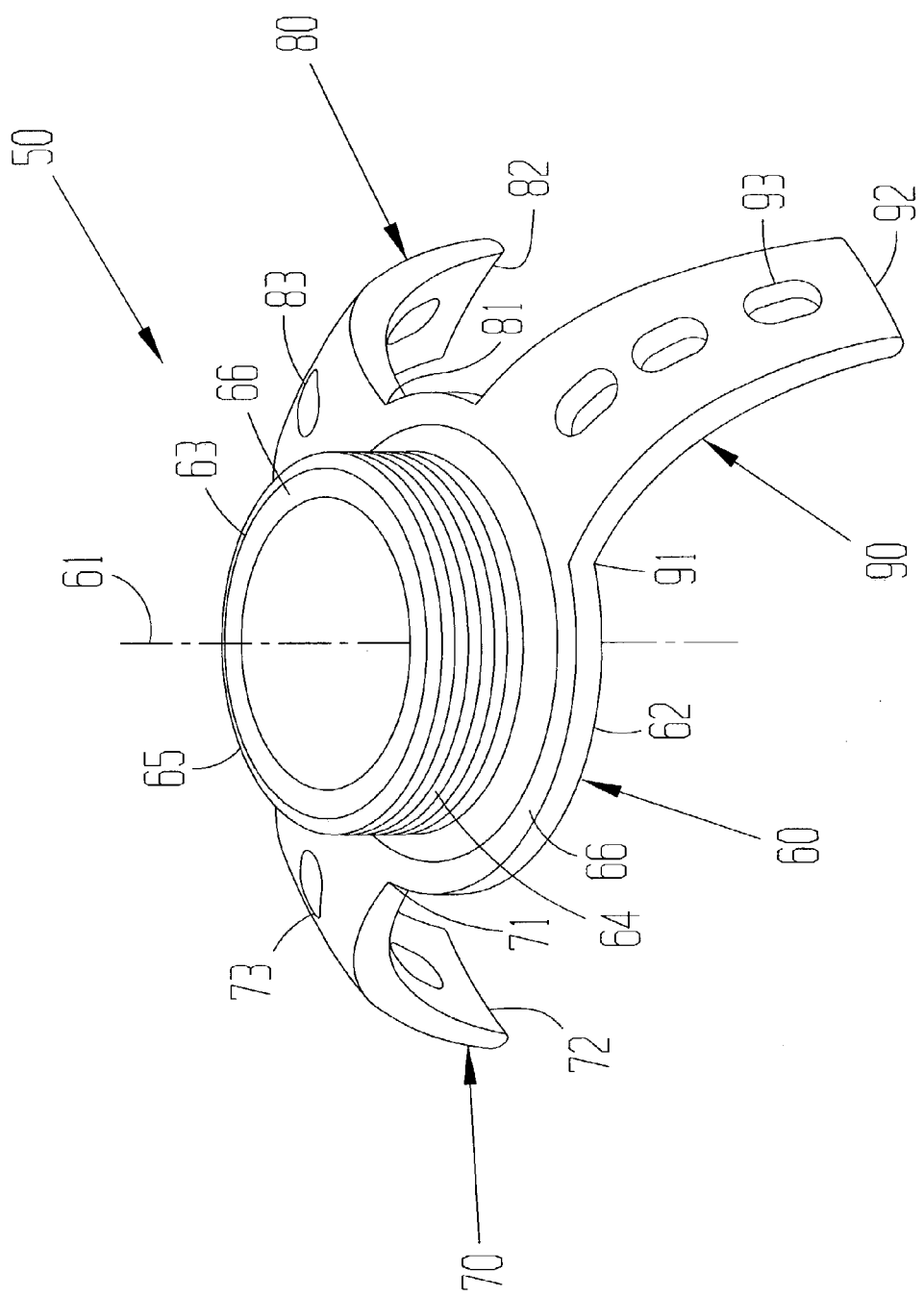
FIG. 4 is a perspective view of the three prong adapter of the present invention, showing the hub second end having a threaded outer surface.

The three prong adapter 50 of the present invention is adapted to be connected to a socket 10, as shown in FIGS. 2 and 3. In this regard, the three prong adapter 50 is positioned next to the socket 10 to determine whether the three prong adapter 50 needs to be manipulated to fit properly with the socket 10. In a given application, any or all of the prongs 70, 80 or 90 may need to be manipulated to better fit with a particular socket 10. Stated more particularly, one or more of the respective free ends 72, 82 and 92 of the prongs 70, 80 and 90 may need to be bent with respect to the connected ends 73, 83, and 93.

Internal stresses are developed within the three prong adapter 50 while bending the prongs 70, 80 and 90. However, due to the circumferentially continuous portion 66 of the hub 60, those stresses do not distort the threads 65 on the surface 64 of the second end 63 of the hub. That is, the circumferentially continuous portion 66 of the hub 60 stops the stresses from propagating to the threads 65. Hence, the threads 65 and surface 64 remain distortion free, even after manipulation of one or more prongs 70, 80 and 90.

A laminate, screws, a combination of both or a different fastener can be used to connect the three prong adapter 50 to a socket 10. Any of the many available and widely understood laminates can be used. When securing the three prong adapter 50 to the socket 10, the hub first end 62 is in direct contact with the laminate. In a preferred embodiment, where both the first and second ends 62 and 63 of the hub 60 are circumferentially continuous, the circumferentially continuous first end 62 separates the threads 65 on the second end 63 from the first end 62. This prevents the laminate from contacting and bonding to the threads 65. This is because the laminate will tend to set rather than flow a distance to the threads. Also, locating the threads 65 on the outer surface 64 provides added protection preventing the laminate from contacting and bonding to the threads. Thus, the threads 65 remain unimpaired by the laminate.

Figure 15:
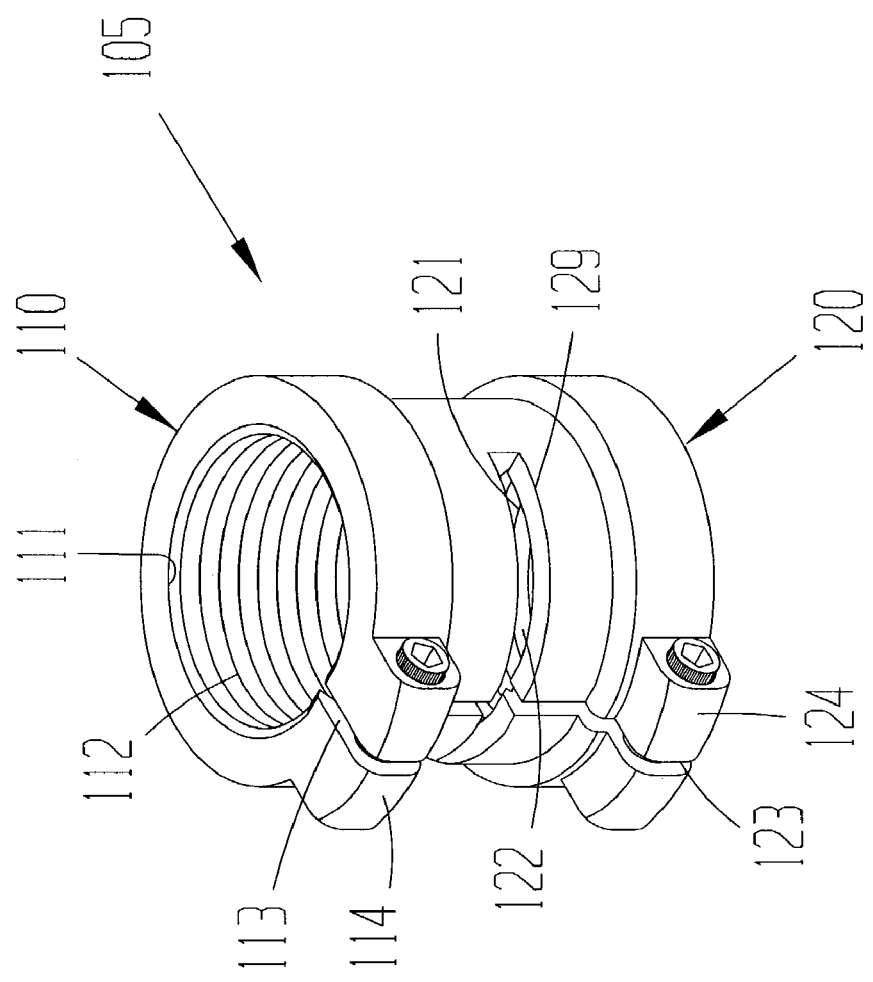
FIG. 15 is a perspective view of a prosthetic component.

In accordance with another aspect of the present invention, shown in FIGS. 2, 3 and 15, a first prosthetic component 105 is provided. The first prosthetic component 105 is preferably made of a titanium alloy or steel. However, other strong yet light materials can be used without departing from the broad aspects of the present invention. The first prosthetic component 105 is preferably made with a precision CNC machining process.

The prosthetic component 105 has a first end 110. The first end 110 has a hole 111 with a threaded inner surface 112. The hole 111 and threaded inner surface 112 have a predetermined circumference. A partition 113 splits the threaded inner surface 112. A clamp 114 is connected to the outer surface of the first end 110. The clamp 114 can be used to selectively reduce the circumference of the hole 111.

The first prosthetic component 105 also has a second end 120. Like the first end 110, the second end has a hole 121 with a threaded inner surface 122. The hole 121 and threaded inner surface 122 have a predetermined circumference. A partition 123 splits the threaded inner surface 122. A clamp 124 is connected to the outer surface of the second end 120. The clamp 124 can be used to selectively reduce the circumference of the hole 120. A slit 129 partially separates the first and second ends 110 and 120. In this regard, the first and second ends 110 and 120 can be independently constricted by clamps 114 and 124, respectively.

The first prosthetic component 105 is adapted to threadably mate, or connect, with the three prong adapter 50 of the present invention, as shown in FIGS. 2 and 3. Stated more particularly, the threaded surface 112 of the first end 110 of the prosthetic component 105 mates with the threads 65 on the outer surface 64 of the hub second end 63. The prosthetic component 105 can be threaded a predetermined amount onto the three prong adapter 50 up to a length equal to the thread length of the hub second end 62. When the prosthetic component 105 is threaded onto the hub second end 63 the desired amount, the clamp 114 is tightened to secure the prosthetic component 105 in place. In this regard, the prosthetic component 105 position can be easily adjusted by loosening the clamp 114.

In this preferred embodiment, it is observed that the combination of the three prong adapter 50 and first prosthetic component 105 provides an identical function of the existing three prong adapter 20, but eliminates the undesirable problems associated with the existing three prong adapters. In this regard, the combination of the three prong adapter 50 and first prosthetic component 105 can be used with all components that currently are used with the existing three prong adapter 20.

One well known existing component is a pylon 130. The pylon can have a fixed receiver 131. Another well known component is a rotatable pyramidal adapter 135. The rotatable pyramidal adapter 135 has a threaded end 136 with a threaded outer surface, and a pyramidal end 137. The fixed receiver 131 is adapted to receive and connect to the pyramidal end 137 of the rotatable pyramidal adapter, as shown in FIG. 2. The rotatable pyramidal adapter 135 can be threaded into the second end 120 of the first prosthetic component 105. Clamp 124 can be tightened to secure the pyramidal adapter 135 in place. Then, the pylon 130 can be connected to the rotatable pyramidal adapter 135, which can be done in a conventional manner.

An alternative three prong adapter embodiment 150 is provided in accordance with yet another aspect of the present invention. The three prong adapter 150 is preferably made of titanium alloy or stainless steel. Yet, other strong yet light materials could be used without departing from the broad aspects of the present invention. The three prong adapter 150 is preferably made in a CNC machining process.

As shown in FIGS. 11–14, the three prong adapter 150 has a hub 160 defining a central axis 161. The hub has a first end 162 and a second end 163. The hub first end 162 is circumferentially continuous. The hub second end 163 is hollow and has an inner surface 164. Threads 165 are on the inner surface 164 of the hub second end 163. A partition 166 is through the second end 163. One or more slits 167 are through a portion of the hub 160. The slits 167 partially separate the first end 162 from the second end 163. The partition 166 causes the second end 163 to not be circumferentially continuous. In contrast, at least one portion of the hub first end 162 is a circumferentially continuous portion 169 of the hub 160.

In a preferred embodiment of the three prong adapter 150, the hub second end 163 has an inner diameter of approximately 1.5 inches. However, other inner diameters can be used without departing from the broad aspects of the present invention. The threads 165 wrap around the inner surface 164 approximately seven or eight times, but could wrap more or fewer times. In this regard, the preferred thread length is preferably approximately 0.3 inches. However, the thread length could be longer or shorter as desired without departing from the broad aspects of the present invention.

The slits 167 allow the hub second end 163 to be flexible in directions generally perpendicular to the hub central axis 161, while the circumferentially continuous first hub end 162 remains generally rigid. A clamp 168 is located on the outside of the hub second end 163. The hub second end 163 has a predetermined circumference, and the clamp 168 can be used to selectively reduce the circumference of the hub second end.

The three prong adapter 150 has a plurality of prongs 170. Prongs 170 are similar to prongs 70, 80, and 90 of three prong adapter 50. Prongs 170 are preferably integral with the hub first end 162. One or more holes can be through each prong 170, and each prong has a connected end and a free end, or distal end. Just like prongs 70, 80, and 90, the prongs 170 are arcuate shaped and can have either squared or rounded free ends. There are preferably three prongs 170, and they are preferably oriented around the hub 160 similarly to how prongs 70, 80 and 90 are oriented around hub 60 of three prong adapter 50.

The three prong adapter 150 is connectable to a socket 10. Sometimes, one or more of the prongs 170 need to be manipulated, or bent, to better fit with the socket 10. This is accomplished similarly to bow prongs 70, 80, and 90 are bent. Internal stresses can develop during the bending of the prongs 170. Yet, those stresses are not propagated through the circumferentially continuous first end 162 of the hub. Therefore, the threads 165 on the inner surface 164 of the hub second end 163 remain distortion free, even after one or more prongs 170 are bent.

A laminate, screws, a combination of both or another fastener can be used to connect the three prong adapter 150 to the socket 10. The circumferentially continuous first hub end 162 acts as a barrier that prevents the laminate from flowing to the threads to contact and bond with them. This is because the laminate is more likely to set that to flow to the threads 165.

The three prong adapter 150 is a direct replacement for an existing three prong adapter 20. In this regard, no additional components are necessary. For example, a rotatable pyramidal adapter 135 simply and directly thread into the hub second end 163. The clamp 168 can then secure the threadably mated pyramidal adapter 135 in place.

Thus it is apparent that there has been provided, in accordance with the invention, an three prong adapter that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A three prong adapter used to connect a prosthetic device to a socket comprising:
   A. a hub defining a central axis and having:
      i. a first hub end; and
      ii. a second hub end having a threaded surface,
   wherein at least one of said first hub end and said second hub end has a circumferentially continuous portion;
   B. a first prong having a first prong first end connected to said first hub end and a first prong second end, wherein said first prong second end is manipulable with respect to said first prong first end;
   C. a second prong having a second prong first end connected to said first hub end and a second prong second end, wherein said second prong second end is manipulable with respect to said second prong first end; and
   D. a third prong having a third prong first end connected to said first hub end and a third prong second end wherein said third prong second end is manipulable with respect to said third prong first end,
   whereby said threaded surface of said hub second end remains distortion free even after manipulation of any of said first prong second end, said second prong second end and said third prong second end.

2. The three prong adapter of claim 1 wherein:
   A. said first prong second end is squared;
   B. said second prong second end is squared; and
   C. said third prong second end is squared.

3. The three prong adapter of claim 1 wherein:
   A. said first prong second end is rounded;
   B. said second prong second end is rounded; and
   C. said third prong second end is rounded.

4. The three prong adapter of claim 1 wherein each of said first prong, said second prong and said third prong have at least one hole therethrough.

5. The three prong adapter of claim 1 wherein said first prong is located diametrically opposite of said third prong around said hub first end, and said second prong is located intermediate between said first prong and said third prong around said hub first end.

6. The three prong adapter of claim 1 wherein said threaded surface of said hub second end has a predetermined thread length.

7. The three prong adapter of claim 6 wherein said predetermined thread length is approximately 0.3 inches.

8. The three prong adapter of claim 1 wherein said first prong, said second prong, and said third prong are each generally arcuate shaped.

9. The three prong adapter of claim 1 wherein said hub second end is circumferentially continuous.

10. The three prong adapter of claim 9 wherein said threaded surface of said hub second end is a threaded outer surface.

11. The three prong adapter of claim 10 wherein said threaded outer surface of said hub second end is a continuously threaded outer surface.

12. The three prong adapter of claim 1 wherein said hub first end is circumferentially continuous.

13. The three prong adapter of claim 12 wherein:
   A. said hub second end has a threaded inner surface; and
   B. at least one slit partially through said hub separates said hub first end and said hub second end.

14. In combination:
   A. a socket for engaging a stump of a limb;

B. an adapter comprising:
  i. a hub having a hub first end and a hub second end, said hub second end having a threaded outer surface; and
  ii. a plurality of manipulable prongs connected to said hub first end and being connectable to said socket;
C. a first prosthetic device threadably connectable to said threaded outer surface of said hub second end; and
D. a means for connecting said adapter to said socket.

15. The combination of claim 14 wherein said plurality of prongs comprises three prongs.

16. The combination of claim 14 wherein:
A. said hub has a central axis; and
B. said plurality of prongs comprises a plurality of independent arcuate prongs that curve in respective directions that approach becoming parallel with said hub central axis as said plurality of independent arcuate prongs move away from said hub.

17. The combination of claim 16 wherein said plurality of arcuate prongs each have a squared distal end.

18. The combination of claim 16 wherein said plurality of arcuate prongs each have a rounded distal end.

19. The combination of claim 14 wherein said hub second end is circumferentially continuous.

20. The combination of claim 19 wherein said threaded outer surface of said hub second end is continuously threaded.

21. The combination of claim 14 wherein said threaded outer surface of said hub second end has a predetermined thread length.

22. The combination of claim 21 wherein said predetermined thread length is approximately 0.3 inches.

23. In combination:
A. a socket for engaging a stump of a limb;
B. an adapter comprising:
  i. a hub having a hub first end and a hub second end, said hub second end having a threaded outer surface; and
  ii. a plurality of manipulable prongs connected to said hub first end and being connectable to said socket; and
C. a first prosthetic device having a first side having a first side threaded hole that is threadably connectable to said threaded outer surface of said hub second end and a second side having a second side threaded hole for threadably receiving a second prosthetic device.

24. A method of constructing a prosthetic limb comprising the steps of:
A. providing a residual limb terminating as a stump;
B. providing a socket adapted to receive the stump of the residual limb;
C. providing an adapter having a plurality of prongs, a circumferentially continuous portion and bore having a threaded inner surface, and that is adapted to connect to the socket;
D. providing a first prosthetic device adapted to be threadably connected to the threaded inner surface of the bore;
E. manipulating at least one of the plurality of prongs and having the circumferentially continuous portion of the adapter prevent the threaded surface of the adapter from distorting in response to the manipulation of at least one of the prongs;
F. connecting the adapter to the socket; and
G. threadably connecting the first prosthetic device to the threaded inner surface of the bore.

25. The method of claim 24 wherein:
A. the step of providing an adapter comprises the step of providing an adapter having a clamp; and
B. the method of constructing a prosthetic limb further comprises the step of tightening the clamp to secure the first prosthetic component in place.

\* \* \* \* \*